United States Patent [19]
Torrisi et al.

[11] Patent Number: 5,351,281
[45] Date of Patent: Sep. 27, 1994

[54] HANDLING SUPPORT FOR X-RAY SPECTROSCOPIC ANALYSIS

[75] Inventors: Angelo M. Torrisi, 10 Anpell Dr., Scarsdale, N.Y. 10583; Roland Urbano, Tuckahoe, N.Y.

[73] Assignee: Angelo M. Torrisi, Scarsdale, N.Y.

[21] Appl. No.: 47,315

[22] Filed: Apr. 15, 1993

[51] Int. Cl.⁵ .......................................... G01N 23/20
[52] U.S. Cl. ...................................... 378/79; 378/45; 378/47; 378/208
[58] Field of Search ....................... 378/45, 47, 79, 208

[56] References Cited

U.S. PATENT DOCUMENTS

| | | | |
|---|---|---|---|
| 3,378,684 | 4/1968 | Mentink et al. | 378/47 X |
| 3,409,769 | 11/1968 | McKinney et al. | 378/47 |
| 4,037,109 | 7/1977 | Hosokawa et al. | 378/45 |
| 4,575,869 | 3/1986 | Torrisi et al. | 378/47 |
| 4,587,666 | 5/1986 | Torrisi et al. | 378/45 X |
| 4,698,210 | 10/1987 | Solazzi | 378/45 X |
| 4,974,244 | 11/1990 | Torrisi et al. | 378/45 |
| 5,253,280 | 10/1993 | Mizuta | 378/45 |

*Primary Examiner*—David P. Porta
*Attorney, Agent, or Firm*—Paul J. Sutton

[57] ABSTRACT

A double open-ended sample holder for sample material for X-ray spectroscopic analysis including a cylindrical body containing the sample material and having top and bottom open faces. An analytic film is mounted tautly across the lower face, and a microporous film positioned across the upper face cell passes gases generated by X-rays striking the sample material but does not pass harmful particle materials contained in the cell. Upper and lower rings mounted to the cylindrical body secure the lower and upper films to the body. A handling support connected to the top securing ring provides a grip for a tool used in the process of remotely raising or lowering the sample holder relative to placement into or removal from an X-ray cassette. The handling support is spaced from the microporous film so that gases generated in the cell are allowed to escape across the microporous film at a maximum rate of evacuation.

9 Claims, 9 Drawing Sheets

HANDLING SUPPORT FOR X-RAY SPECTROSCOPIC ANALYSIS

FIELD OF THE INVENTION

This invention relates generally to the field of disposable sample holders for X-ray spectroscopic analysis and more particularly to a handling support for safe and efficient handling of the sample holders.

BACKGROUND OF THE INVENTION

The field of X-ray spectroscopy involves the measurement of the spectra of certain material being analyzed. Generally, the sample material being analyzed may be any liquid, slurry, powder material, or industrial gas that can occur in the run of industry. A sample is positioned in a cylindrical sample holder that includes a holder body forming a cell adapted to contain the sample. A disposable sample holder is generally made of plastic and is generally disposed of after a single use. A sample holder generally ranges in size between diameters of 20 to 57 mm and in height about 25 to 35 mm.

Sample holders include single open-ended cylindrical body type cells and double open-ended cylindrical body cells. For the double open-ended cell, a very thin plastic analytic film is placed as an X-ray transparent window across one of the circular end faces of the body of the holder, and the skirt of the film is then secured by a plastic securing ring to the outer wall of the body and the analytic film becomes taut. The body is then inverted so that the window face is positioned downwards. Alternatively, the plastic securing ring and the thin plastic analytic film is placed into a well of a sample holder film assembly device and one of the circular end faces of the holder body is placed over the film and the skirt of the film is then secured by the plastic ring to the outer wall of the body so that the analytic film becomes taut. The latter method is described in our Pat. No. 4,587,656. It is noted that the plastic securing rings are made of a thin, plastic, flexible material so that the thin analytic film can be gently yet firmly secured to the sample holder body. A double open-ended sample holder is illustrated in FIGS. 1 and 2 and discussed in relation therewith below.

In each of the above-described assembly methods, one circular end face is open so as to form a holder cell. The holder cell is then filled with the sample through the top open face of the cell. The sample may be a benign substance or it may be noxious, contaminated, caustic, or offensive. In addition, the sample may be treated with a solvent to dissolve the sample, the solvent itself being noxious.

After the sample material to be analyzed has been loaded into the sample cell and otherwise prepared for X-ray analysis, the cell is loaded into an X-ray sample cassette that is then moved into position for bombardment by X-rays. X-ray cassettes are cylindrical holders defining chambers into which the sample holder cell is loaded. Generally, the chambers of the cassettes have top edges that are of greater height than the height of the top edges of the sample holder cells. In addition, the diameters of the cassettes are generally only slightly greater than the diameters of the sample holders so that little space is provided between the wall of the cassette and the wall of the sample holder. Cassettes often have a spring-loaded screw-on cap over the cell.

In the present state of the art, a double open-ended sample holder is loaded into an X-ray cassette by hand by a technician. More in detail, the double open-ended cell is picked up by the technician, who may or may not be wearing protective gloves, transferred to a position above the cassette, and hand placed into the cassette. Also, the cassette may be located for loading purposes in an isolation chamber in which the double open-ended sample holder is placed into the cassette by a technician who manipulates the holder with flexible gloves that extend into the chamber.

In the process of X-ray analysis, when X-rays are directed at the bottom end of the cell body through the analytic film at the sample inside; the X-ray cause heat to be generated within the sample material. Many substances will not generate gases or vapors, or if they do so, such gases or vapors may be harmless to the X-ray equipment or the immediate environment. Certain sample substances, usually a liquid but at times a powder, upon heating will generate a vapor or a gas containing particles originating from the sample substance that should not be allowed to contaminate the X-ray machine or pass into the surrounding area. In such cases, the upper open face of the cell body must be covered to prevent passage of such contaminants. A problem exists, however, in that simple covering of the open face with a sheet of plastic film secured by a securing top ring or by a plastic cap will result in the sealing of the cell body so that a buildup of pressure within the cell body will occur upon generation of vapors therein. Such a pressure buildup will result in the bottom analytic film bulging outwardly from the cell along with the sample material thus distorting the entire process of the X-ray analysis.

In such cases where a top seal of the sample holder is required to prevent passage of vapor borne contaminants, a microporous film is secured across the top face of the cell body secured thereto by an upper securing ring. The microporous film will pass gases generated by the heated sample material but will filter out particles that would cause harm to the surrounding environment.

Microporous film is a gas permeable material, generally polypropylene or teflon, specifically intended to establish and maintain pressure equalization within a sample holder cell. Such film is characterized with the property of containing tortuous submicron-size passageways extending from one surface side to the other. This permits gases and vapors to permeate yet simultaneously prohibits the penetration of particles of the sample substance therethrough. Microporous film enables evacuation of entrapped gases through the micropores while at the same time relieves the sample holder of vapor pressure buildup. Under inert gas conditions such as helium, the micropores function as passageways for the gas to enter the sample holder cell and purge out any entrapped gases or vapors. In atmospheric operating conditions, the film helps maintain pressure equalization by continuously allowing the exchange of contained gases with the surrounding air environment. In all cases the immediate important consideration is to maintain a taut, thin-film sample support plane that defines the surface of the contained solution or powdered sample material. Any distension or convolution of the thin-film substance affects the sample-to-excitation source distance implying higher or lower than actual analytic concentration values.

In each of these cases the sample cell holder is in effect dropped into the cassette. This procedure is undesirable since the entire handling procedure for sample analysis requires gentle handling of the sample throughout the entire procedure of X-ray analysis, which includes gentle placement of the sample cell into the cassette.

Even greater problems occur with the removal of the sample holder cell from the X-ray cassette after the X-ray analysis. When the sample substances are noxious or offensive, spilling of the substances during removal of the cell from the cassette and during its transit to either a waste disposal station or to a recovery station often has undesirable results.

Remote handling caps for sample holders exist in the art, but not for microporous film covered holders. For example, our U.S. Pat. No. 4,575,869 describes a sample holder that includes a handling support for safe handling of the sample holder by either local or remote means. This handling support does not cover the case of a double open-ended cell where the top face of the cell must be covered by a microporous film. The top wall of remote handling caps also would be in proximity or in contact with the microporous film so that the integrity of the microporous film would be compromised.

SUMMARY OF THE INVENTION

The present invention contemplates a double open-ended sample holder for X-ray spectroscopic analysis of sample materials contained therein that have the top open end of the sample holder covered by a microporous film that overcomes the limitations and disadvantages of the prior art by providing a double open-ended sample holder with a handling support that meets the special needs of handling double open-ended sample cell holders directly by a technician with a remote handling tool (tweezers), or by a remote precision handling tool (a robot).

It is therefore an object of the present invention to provide a double open-ended sample holder containing sample material requiring a microporous film that allows gentle or remote handling of the sample holder relative to its placement into or removal from an X-ray cassette.

It is another object of the present invention to provide a double open-ended sample holder having a microporous film mounted across its top open face that includes a remote handling support that allows the microporous film to pass gases generated in the cell at a maximum rate of evacuation but prevents passage of harmful materials.

In accordance with these and other objects that will become apparent in the course of this disclosure, there is provided a double open-ended sample holder for sample material for X-ray spectroscopic analysis including a cylindrical body cell containing the sample material and having top and bottom open faces. An analytic film is positioned across the lower face and a microporous film positioned across the upper face cell passes gases generated by X-rays striking the sample material but does not pass harmful materials contained in the cell. Upper and lower rings mounted to the cylindrical body secure the lower and upper films to the body. A handling support connected to the top securing ring provides a grip for a tool used in the process of remotely raising or lowering the sample holder relative to placement into or removal from an X-ray cassette. The handling support is spaced from the microporous film so that gases generated in the cell are allowed to escape across the entire area of the film at a maximum rate of evacuation.

The present invention can be better understood and the objects and important features, other than those specifically set forth above, will become apparent when consideration is given to the following details and description, which when taken in conjunction with the annexed drawings, describes, discloses, illustrates, and shows preferred embodiments or modification of the present invention and what is presently considered and believed to be the best mode of practice in the principles thereof.

A BRIEF STATEMENT OF THE FIGURES

DETAILED DESCRIPTION OF THE PREFERRED EMBODIMENT

Reference is now made in detail to the drawings wherein the same numerals refer to the same or similar elements throughout.

Figure 1:
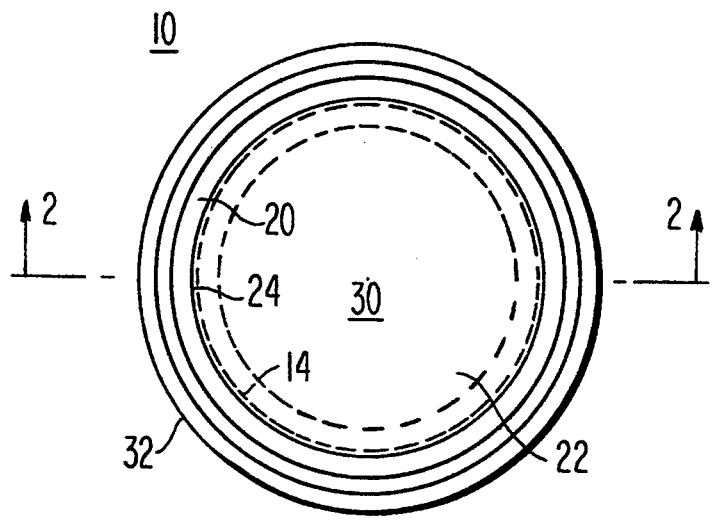
FIG. 1 illustrates a prior art double open-ended sample holder in a top view.
Figure 2:
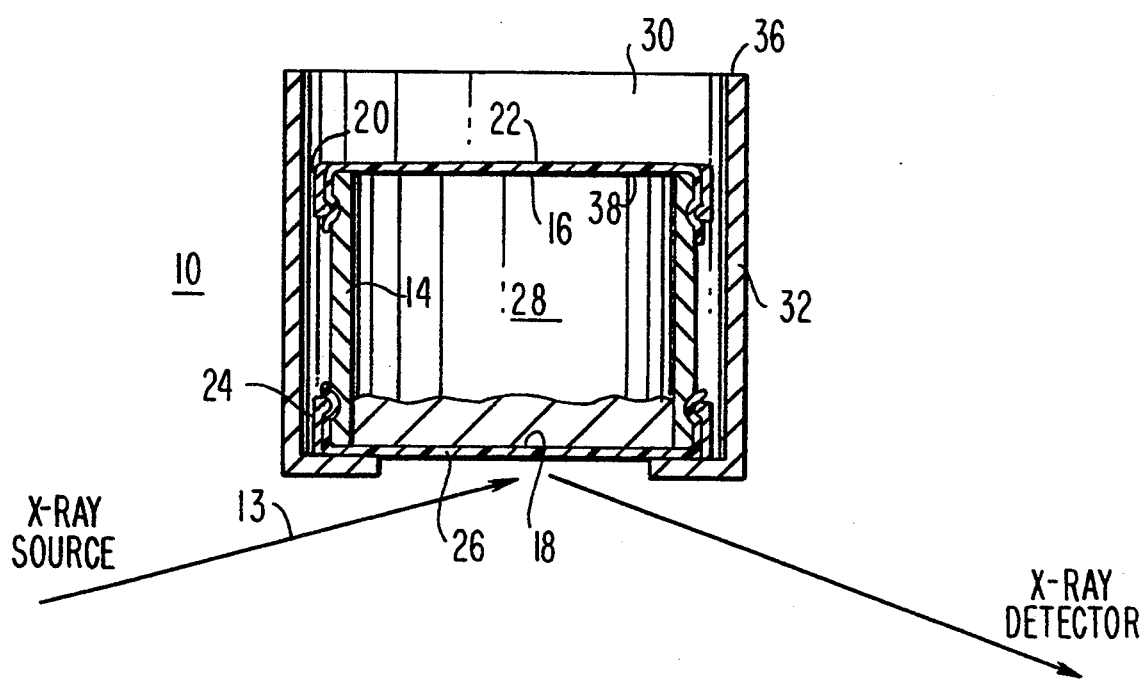
FIG. 2 is a sectional view taken through line 2—2 of FIG. 1.

A prior art double open-ended sample holder 10 holding sample material 12 which can be a liquid or powder, shown here as a powder, for X-ray spectroscopic analysis is illustrated in FIGS. 1 and 2. Sample material 12 is of a nature that X-rays 13 generate heat therein resulting in the creation of a gas containing contaminants that must not be allowed to pass from sample holder 10. At the same time, a pressure buildup in sample holder 10 must be avoided. Sample holder 10 includes a cylindrical wall 14 having a top open face 16 and an opposed bottom open face 18 and an upper cylindrical ring 20 securing an upper thin plastic microporous film 22 to wall 14 across top open face 16 and a lower cylindrical ring 24 securing a lower thin plastic analytic film 26 across bottom face 18 so as to define a sample holder cell 28. Sample holder 10 is positioned in the cylindrical compartment 30 of an X-ray cassette 32 for an X-ray spectroscopic apparatus with X-rays 13 entering through lower analytic film 26 to strike sample material 12 at an angle and returning to the X-ray detector for analysis. Cassette 32 usually has a circular upper rim 36 that is located above the circular upper rim 38 of body wall 14 as shown in FIG. 2, or located at an equal level with upper rim 38. Lowering and raising sample holder 10 into cassette 32 presents a problem of protection of the technician or the X-ray apparatus.

Figure 3:
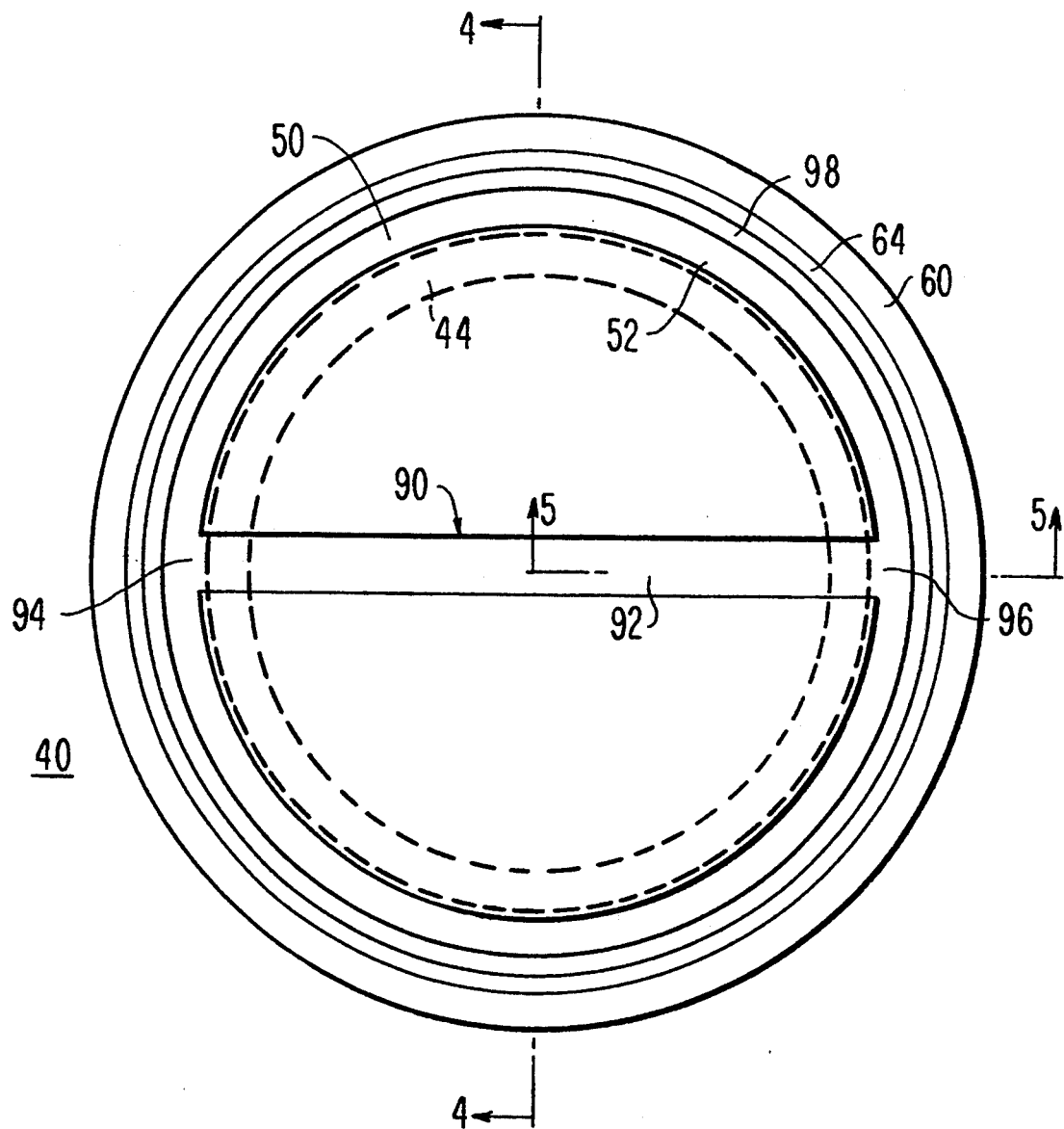
FIG. 3 illustrates a top view of a double open-ended sample holder in accordance with the present invention.
Figure 4:
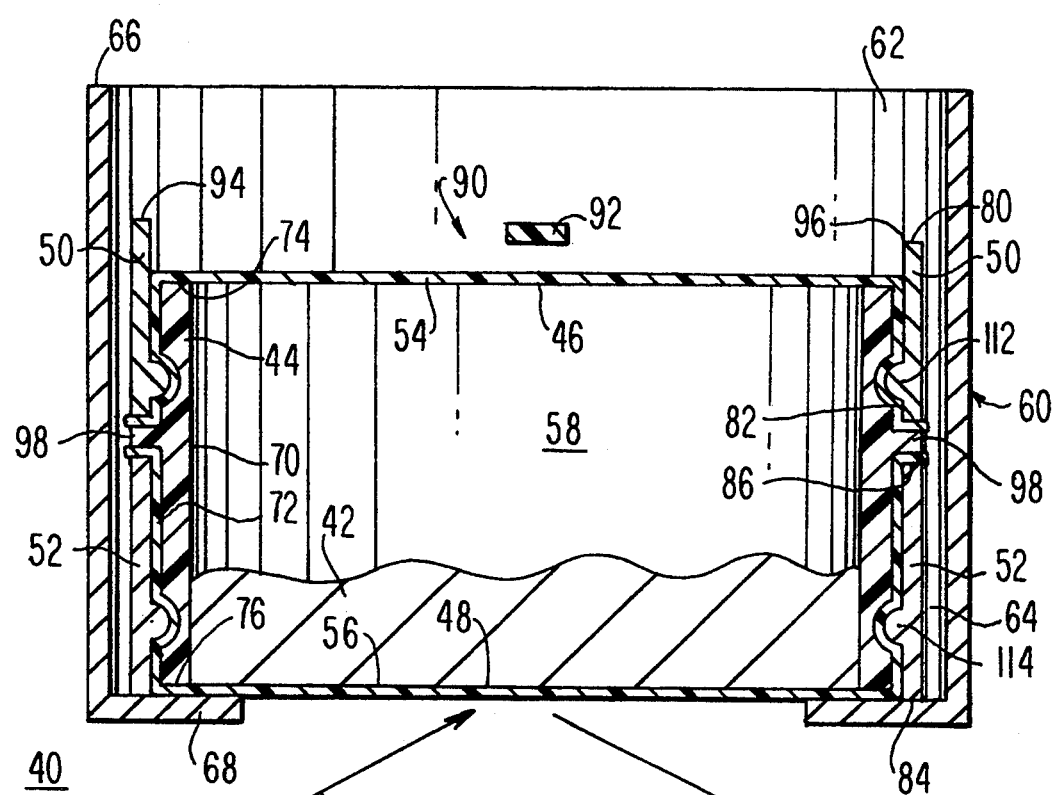
FIG. 4 is a sectional view taken through line 4—4 of FIG. 3.
Figure 5:
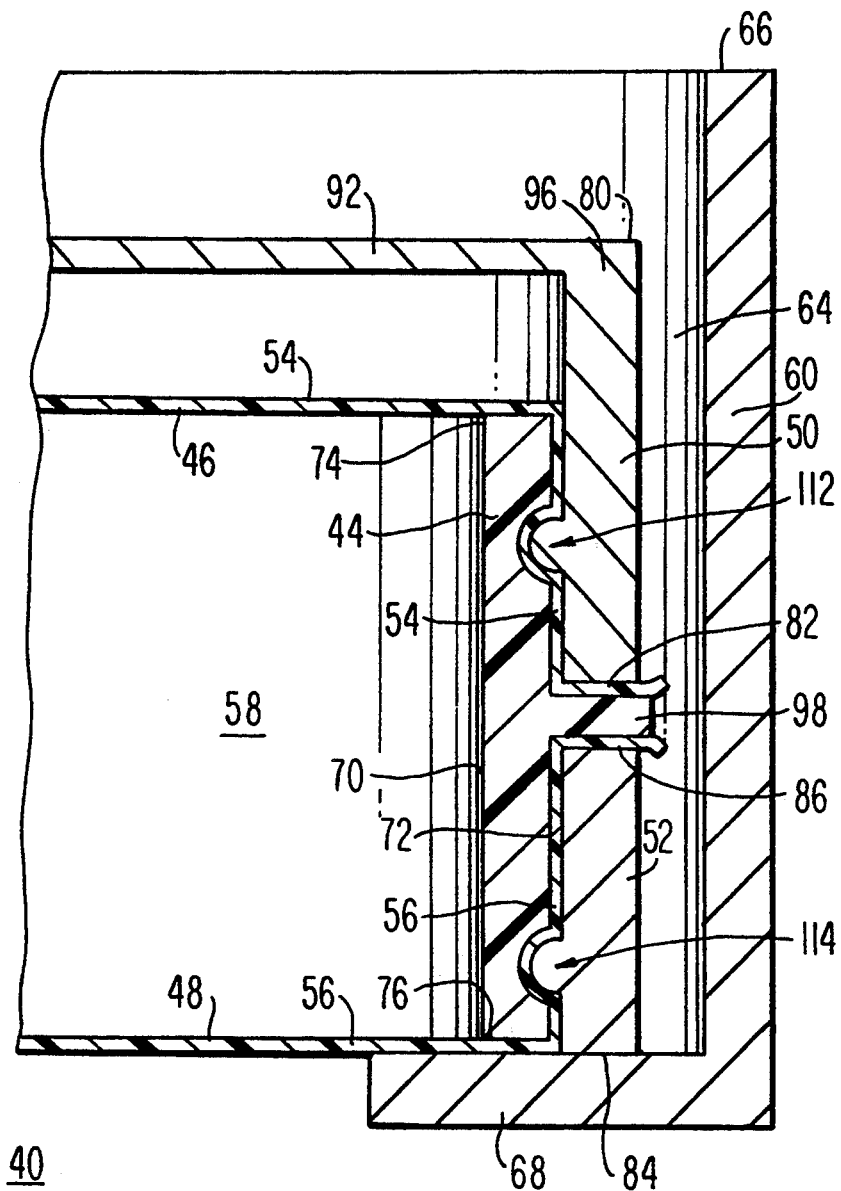
FIG. 5 is a sectional view taken through line 5—5 of FIG. 4.

In accordance with the present invention, a double open-ended sample holder 40 holding sample material 42 which can be a liquid or powder, shown here as a powder, for X-ray spectroscopic analysis is illustrated in FIGS. 3, 4, and 5. Sample holder 40 includes a cylindrical cell wall 44 having a top open face 46 and an opposed bottom open face 48 and an upper cylindrical ring 50 securing an upper microporous film 54 across top open face 46 of cell wall 44 and a lower cylindrical ring 52 securing a lower analytic film 56 tautly across bottom open face 48 of cell wall 44 so as to define a sample holder cell 58. Sample holder 40 is positioned in a cassette 60 for an X-ray spectroscopic apparatus, specifically in the cassette compartment 62, with X-rays 63 entering through analytic film 56 to strike sample material 42 at an angle and returning to the X-ray detector for analysis. Sample holder 40 is positioned in cassette 60 with upper and lower rings 50 and 52 and cassette 60 having a space 64 therebetween. Cassette 60 has a circular upper rim 66 and a circular lower flange 68 extending inwardly from the circular bottom end of cassette 60. Flange 68 has an inner flange diameter that is less than the outer diameter of sample holder 40 so that sample holder 40 rests upon flange 68 when positioned in cassette 60. Flange 68 defines a circular open area across the flange diameter for passage of X-rays 63 to bottom open face 48 of cell wall 44.

Cylindrical cell wall 44 has inner and outer surfaces 70 and and 72, respectively, and opposed circular top and bottom wall rims 74 and 76, respectively, that define opposed top and bottom faces 46 and 48, respectively. Upper microporous film 54, which is positioned across top open face 46 of cell 58, passes gas from cell 58 resulting from heat generated in sample material 42 by X-rays 63 and simultaneously prevents harmful particle materials from passing out of cell 58. Lower analytic film 56 is positioned across bottom open face 48 of cell 58 and lower ring 52 maintains a taut film surface for sample material 42 in contact therewith for X-ray analysis.

Upper ring 50 is mounted to cell wall 44 at outer surface 72. Upper ring 50 has upper ring circular outer and inner rims 80 and 82, respectively. Upper ring outer rim 80 is spaced above circular top wall rim 74. Upper ring 50 mounts microporous film 52 to cell wall 44 wherein microporous film 52 extends across top open face 46 and is pressed between outer surface 72 and the inner surface of upper ring 50. Lower ring 52 mounts analytic film 56 to cell wall 44 wherein analytic film 56 extends across bottom open face 48 and is pressed between outer surface 72 of cell wall 44 and the inner surface of lower ring 54. Lower ring 52 has outer and inner rims 84 and 86, respectively, with outer rim 84 being generally aligned with bottom wall rim 76 and bottom open face 48.

A handling support 90 is connected to upper ring outer rim 80 and spaced above top face 46 of cell 58. Handling support 90 provides a grip for a tool used in the process of gentle placement or removal of sample holder 40 from cassette 60, that is, lowering or raising sample holder 40.

Handling support 90 includes a support bar 92 attached at opposed ends 94 and 96 to upper ring outer rim 80 extending diametrically across and horizontally spaced above top face 46 of cell 58 so that the entire area of microporous film 52 is available to pass gases generated by X-rays 63 striking sample material 42 in cell 58. In addition, support bar 92 is spaced at a distance above microporous film 54 without interfering with the integrity of the face of microporous film 54. In addition, support bar 92 is spaced at a distance above microporous film 54 sufficient to allow a tool to be positioned under bar 92.

A circular stop flange 98 extending outwardly from outer surface 72 of cylindrical cell wall 44 seats upper ring 50 at inner rim 82 relative to cell wall 44 during the mounting process and in addition prevents movement in an axial direction towards bottom face 48 after seating. Stop flange 98 also seats lower ring 52 at inner rim 86 relative to cell wall 44 during the mounting process and in addition prevents axial movement in a direction towards top face 46 after seating.

Inner rim 82 of upper ring 50 is spaced at such a distance from outer rim 80 and is of such a thinness that inner rim 82 is both flexible and resilient so that microporous film 54 can be mounted to said cell wall 44 gently and securely without being damaged or torn. Lower ring 52 has both the flexibility and resilience to gently mount analytic film 56 and to hold analytic film 56 firmly and tautly across bottom face 48. Upper and lower rings 50 and 54 are made of resilient plastic.

Figure 6:
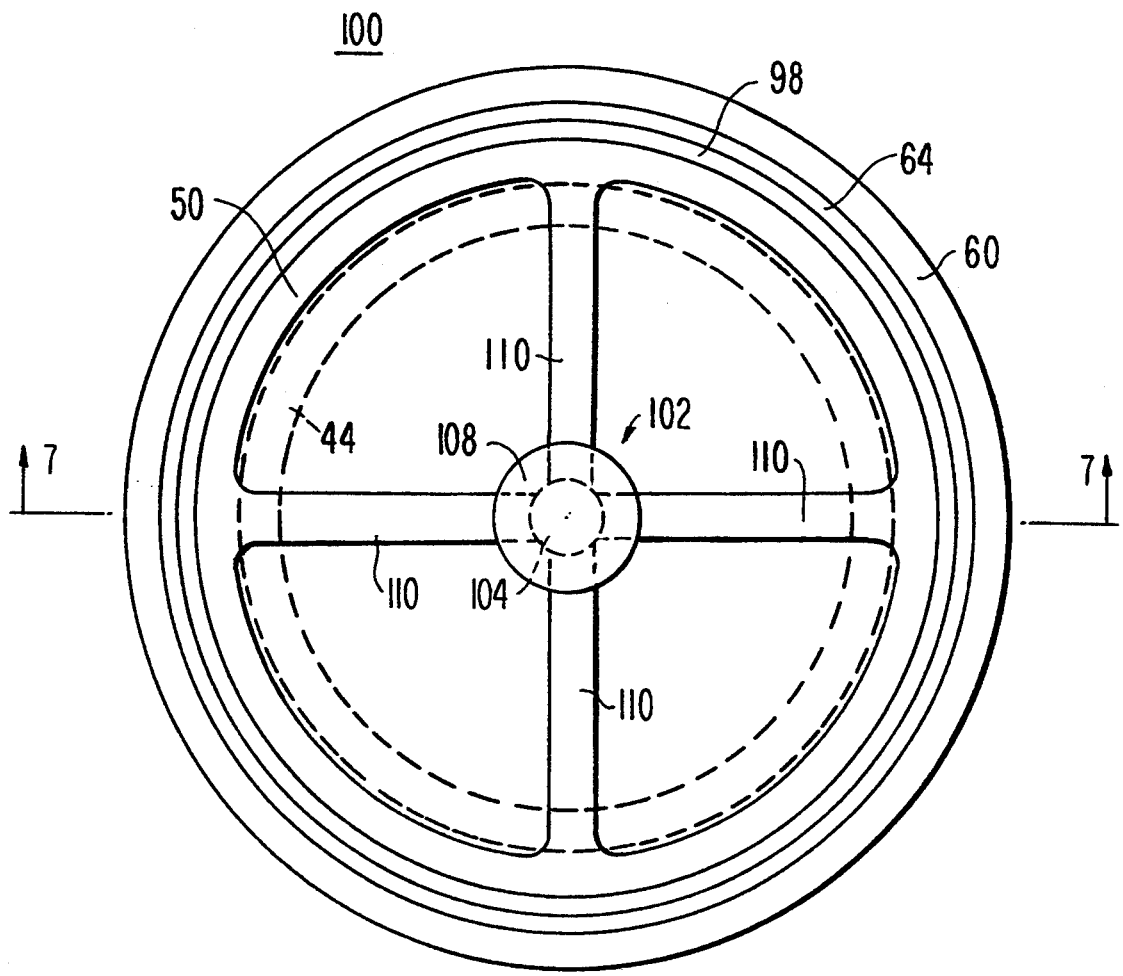
FIG. 6 illustrates a top view of another embodiment of a double open-ended sample holder in accordance with the present invention.
Figure 7:
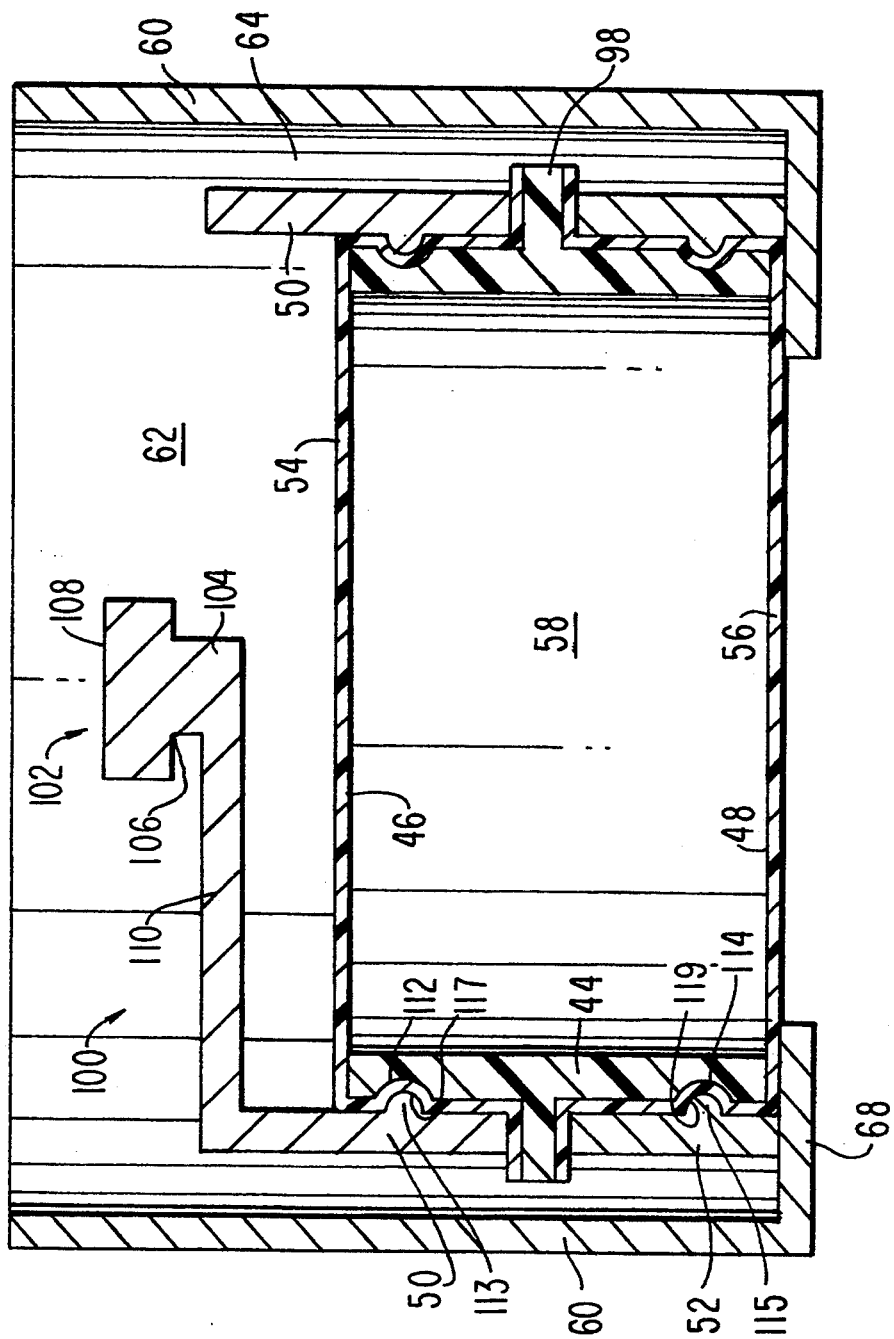
FIG. 7 is a sectional view taken through line 7—7 of FIG. 6.

FIGS. 6 and 7 illustrate another embodiment of the invention that includes a double open-faced sample holder 100 having features analogous to sample holder 40 with similar elements indicated by the same numerals as shown for sample holder 40. Sample holder 100 includes a handling support 102 that includes a cylindrical stem 104 having a top side 106 and a cylindrical disc 108 affixed to top side 106. Disc 108 has a greater diameter than the diameter of stem 104. Disc 108, stem 104, and cell wall 44 are vertically axially aligned. Stem 104 and disc 108 are spaced above top face 46 of cell compartment 58. Four horizontal support struts 110 are connected to and radiate outwardly at equal angles from stem 104 and connect to upper ring outer rim 80. Handling support 102, in particular struts 110, is positioned at a such a distance above top face 46 of cell compartment 58 and microporous film 54 that a maximum area of microporous film 54 is available to pass gases generated by X-rays striking sample material in cell 58 (not shown). In addition, handling support 102 is spaced at such a distance above microporous film 54 so as to receive a lifting tool that will not interfere physically with the integrity of the film face of microporous film 54.

Upper and lower rings 50 and 52 are prevented from axial movement towards top and bottom faces 46 and 48, respectively, by upper and lower circumferential snap-in connections 112 and 114, respectively, each comprising respectively, a circumferential bead 113, 115 about upper and lower ring 50 and 52 respectively, positioned, respectively in a circumferential groove 117, 119 located in outer surface 72 of cell wall 44.

Figure 8:
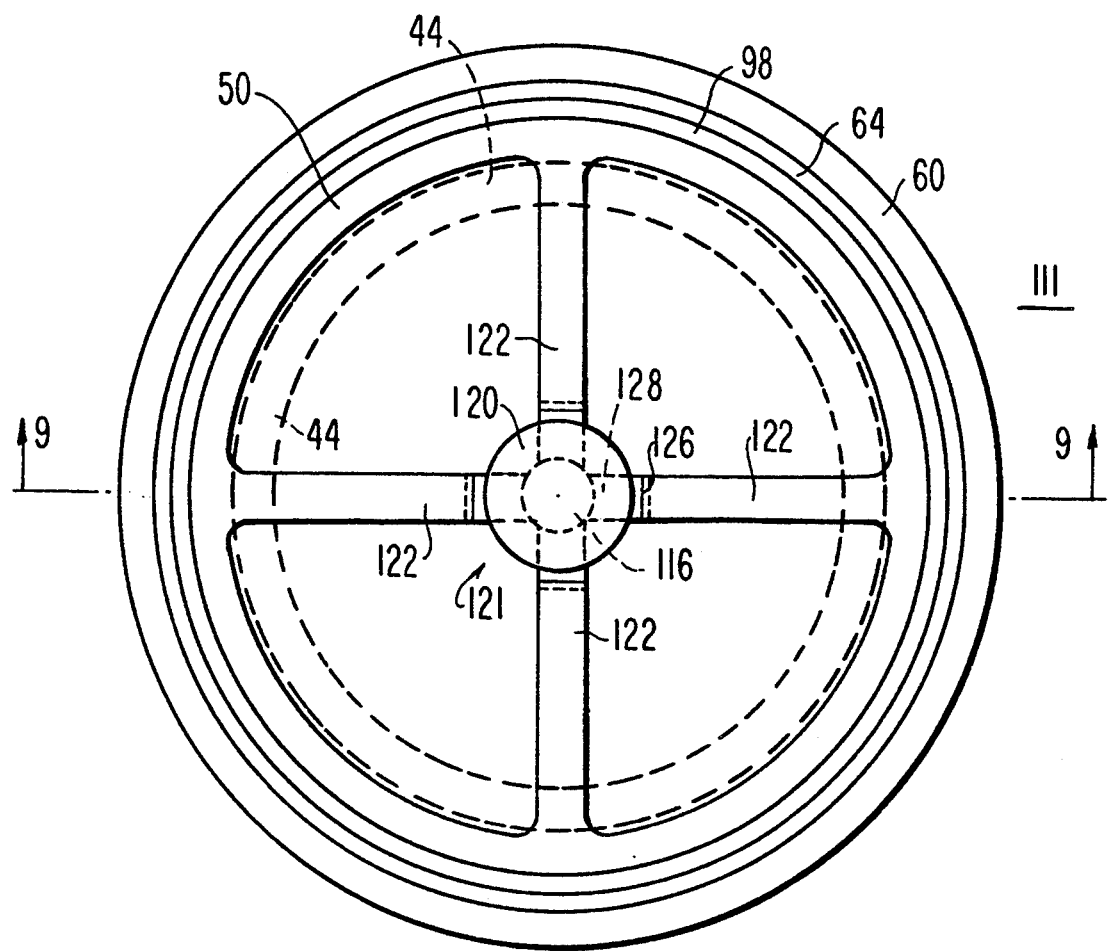
FIG. 8 illustrates a top view of another embodiment of a double open-ended sample holder in accordance with the present invention.
Figure 9:
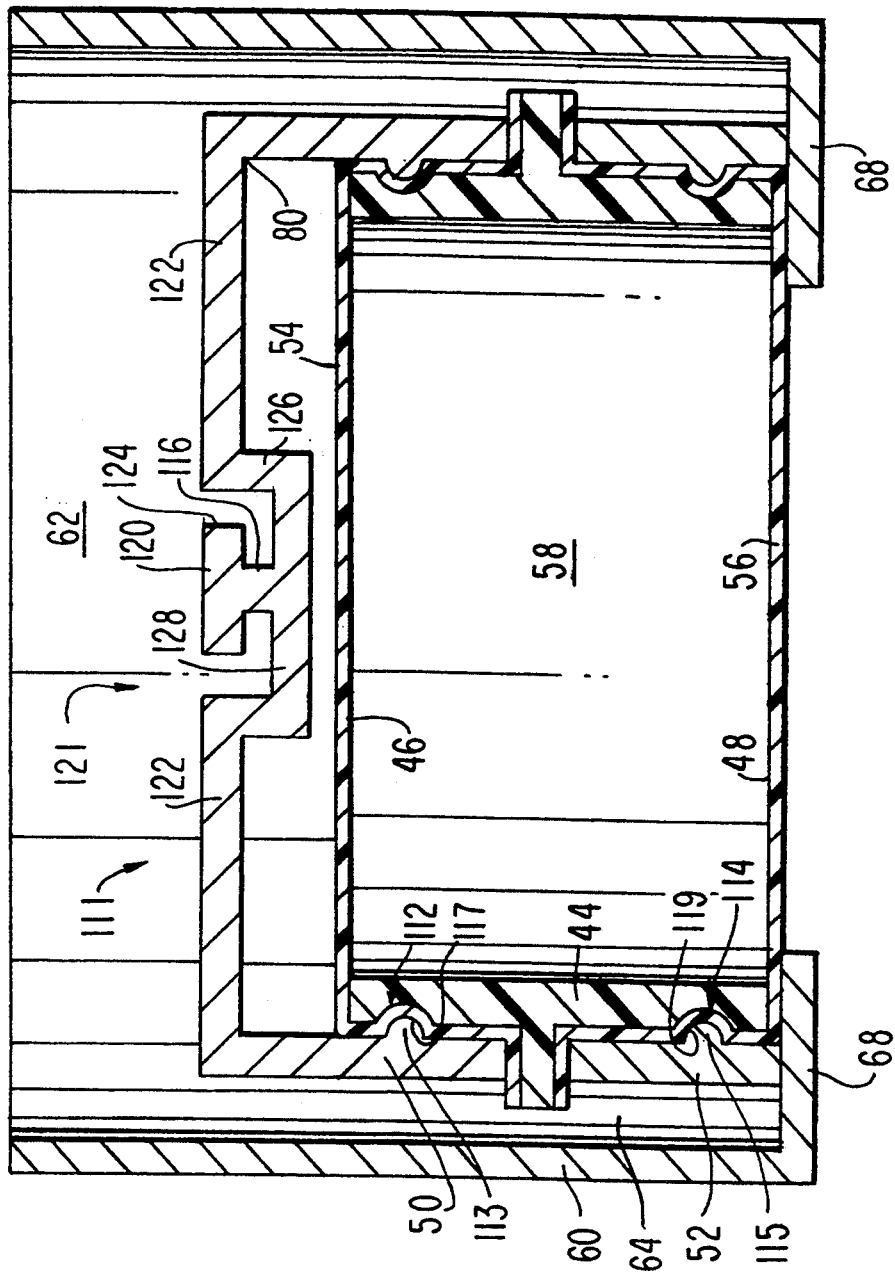
FIG. 9 is a sectional view taken through line 9—9 of FIG. 8.

FIGS. 8 and 9 illustrate another embodiment of the invention that includes a double open-faced sample holder 111 having features analogous to sample holder 100 illustrated in FIGS. 6 and 7 with similar elements indicated by the same numerals as shown for sample holder 100. Sample holder 111 includes a handling support 121 that includes a cylindrical stem 116 having a top side and a cylindrical disc 120 affixed thereto. Disc 120 has a greater diameter than the diameter of stem 116. Disc 120, stem 116, and cell wall 44 are vertically axially aligned. Stem 116 and disc 120 are spaced above top face 46 of cell compartment 58. Four support struts 122 are connected to and radiate horizontally at equal angles from upper ring outer rim 80 to an axial area where struts 122 extend downwardly by way of vertical strut portions 126 to a position spaced above microporous film 54 to form an axially aligned well 124 in which handling support 114 is positioned. Short horizontal tie-in struts 128 connect strut portions 126 with stem 116. Handling support 121, which includes struts 122, well 124 and stem 116 with disc 120 are positioned at a such a distance above top face 46 of cell compartment 58 and microporous film 54 that a maximum area of microporous film 54 is available to pass gases generated by X-rays striking sample material in cell 58 (not shown). In addition, handling support 121 is spaced at such a distance above microporous film 54 so as to receive a lifting tool that will not interfere physically with the integrity of the film face of microporous film 54.

Upper and lower rings 50 and 52 are prevented from axial movement towards top and bottom faces 46 and 48, respectively, by upper and lower circumferential snap-in connections 112 and 114, respectively, each comprising a circumferential bead 113, 115, respectively about upper and lower ring 50 and 52, respectively, positioned in a circumferential groove 117, 119, respectively, defined in outer surface 72 of cell wall 44 adjacent rings 50 and 52, respectively.

Figure 10:
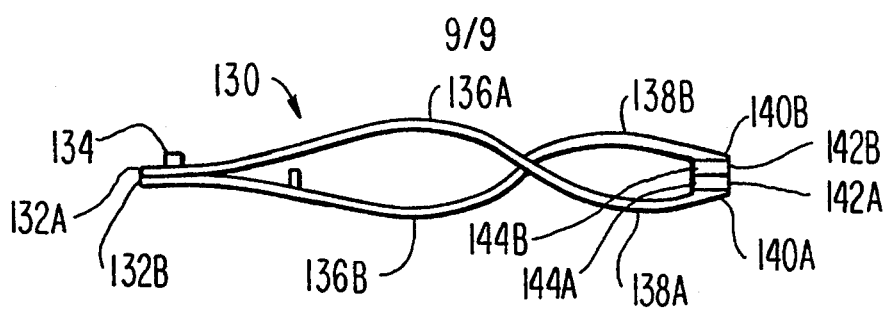
FIG. 10 is a top plan view of a tool for remote handling of the sample holder in accordance with the present invention.
Figure 11:
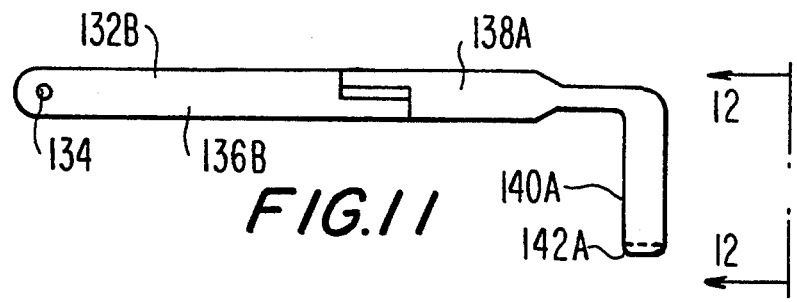
FIG. 11 is a side elevational view of the tool shown in FIG. 10.
Figure 12:
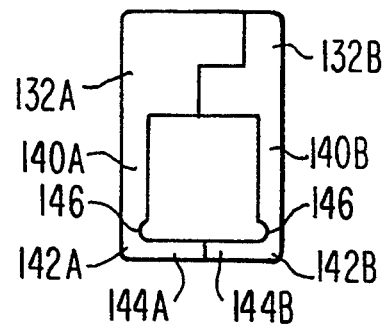
FIG. 12 is an end elevational view of the tool shown in FIG. 11.

FIGS. 10, 11, and 12 illustrate a remote support handling tool, namely, tweezers 130, that can be used to grasp and to lower sample holder 40 into and subsequently to raise sample holder 40 from cassette 60 (see FIG. 4). A pair of opposed, biased horizontal arms 132A and 132B are joined at one end by a rivet 134. Arms 132A and 132B have first outward convolutions 136A and 136B from rivet area 134 then convoluted back in a crossover to second outward convolutions 138A and 138B and then return to opposed vertical fingers 140A and 140B that terminate in pinching portions or Jaws 142A and 142B which have opposed inner shelves 144A and 144B that fit under support bar 92 for lifting sample holder 40 when placing sample holder 40 into cassette 60 or removing sample holder 40 from cassette 60. Opposed cutouts 146 are defined by jaws 142A and 142B at shelves 144A and 144B. When first outward convolutions 136A and 136B are manually or remotely pressed together, jaws 142A and 142B and shelves 144A and 144B are forced apart with arms 132A and 132B in a biased mode. When first convolutions 136A and 136B are released, arms 132A and 132B self-biasedly move to a lesser biased mode so as to hold jaws 142A and 142B together. Support bar 92 lies upon shelves 144A and 144B with the sides of support bar 92 positioned in cutouts 146.

Figure 13:
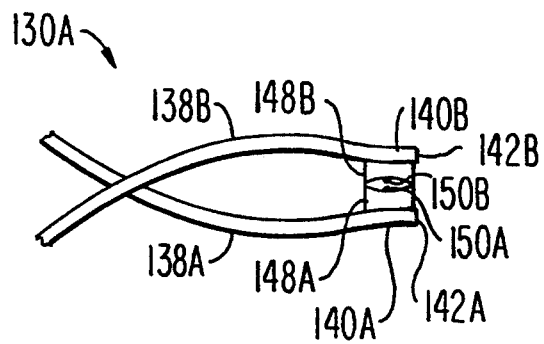
FIG. 13 is a top plan view of the tool shown in FIG. 10 showing an alternative embodiment of the tool.

FIG. 13 illustrates a tweezers 130A that has opposed shelves 148A and 148B that each define a semicircular aperture 150A and 150B and which receive stems 104 and 116 of handling supports 102 and 114. Shelves 148A and 148B are in contact with the underside of discs 108 and 120 so that sample holders 100 and 112 can be raised or lowered by manipulation of tweezers 130A.

Although the present system has been described in some detail by way of illustration and example for purposes of clarity and understanding, it will, of course, be understood that various changes and modifications may be made in the form, details, and arrangements of the parts without departing from the scope of the invention set forth in the following claims.

What is claimed is:

1. A sample holder for a sample material for X-ray spectroscopic analysis, comprising, in combination,
   cell means for containing the sample material and having top and bottom rims defining opposed top and bottom open faces, respectively,
   analytic film means positioned across said bottom open face of said cell means for containing said sample material,
   film securing means for mounting said analytic film means across said bottom open face of said cell means and for maintaining a taut film surface for said sample material for X-ray analysis,
   microporous film means positioned across said top open face of said cell means for passing gases generated by X-rays striking the sample material from said cell means but not passing harmful materials contained in said cell means,
   microporous film securing means for mounting said microporous film means across said top open face of said cell means, and
   handling support means for providing a grip for a tool used in the process of raising or lowering said sample holder without interfering with the integrity of the face of said microporous film means and for allowing concurrently the gases to escape from said cell means at a maximum rate of evacuation through said microporous film means across said top face of said cell means, said handling support means being connected to said microporous film securing means.

2. The sample holder according to claim 1, wherein said cell means includes a cylindrical cell wall having an inner surface forming a cell compartment and an outer surface and a circular top wall rim, and wherein said microporous film securing means is a cylindrical upper ring connected to said cell wall at said outer surface and having an upper ring circular outer rim spaced above said circular top wall rim, said handling support means being connected to said upper ring outer rim and spaced above said top face of said cell compartment and said microporous film.

3. The sample holder according to claim 2, wherein said handling support means is a support bar attached at opposed ends to said upper ring outer rim and extending diametrically across and spaced above said top face of said cell compartment.

4. The sample holder according to claim 2, wherein said handling support means includes a cylindrical stem having a top side and a cylindrical disc affixed to said top side of said disc, said disc having a greater diameter than the diameter of said stem, said disc, said stem, and said cell wall being vertically axially aligned, said stem and said disk being spaced above said top face of said cell compartment; and further includes a plurality of horizontal support struts connected to and radiating outwardly from said stem and connected to said upper ring top rim positioned above said top face of said cell compartment.

5. The sample holder according to claim 4, wherein said plurality of struts defines an axial well, said stem and said disc being positioned in said well.

6. The sample holder according to claim 2, wherein said cell means further includes circular stop means extending outwardly from said outer surface of said cell wall for seating said upper ring relative to said cell wall and for preventing subsequent movement in a direction towards said bottom face of said cell compartment.

7. The sample holder according to claim 6, wherein said stop means is further for seating said lower ring relative to said cell wall and for preventing axial subsequent movement in a direction towards said top face of said cell compartment.

8. The sample holder according to claim 2, wherein said upper ring includes a circular inner rim opposed to said circular outer rim, said circular inner rim being spaced from said outer rim at such a distance that said inner rim is flexible and resilient wherein said microporous top film can be mounted to said cell wall gently and securely without tearing and held securely to said cell wall.

9. The sample holder according to claim 4, further including remote handling means for lifting said handling support means for placement of said sample holder into the cassette and removal of said sample holder from the cassette, said remote handling means including biasable tweezers having a pair of horizontal arms and a pair of vertical fingers connected to said arms, said fingers having bottom jaws having shelves, said shelves being positioned under said handling support means during lifting of said sample holder, said jaws being in a gripping position when said arms are in a partly biased mode, and said jaws being spaced apart in a non-gripping position when said arms are spaced apart in a biased mode, each of said jaws defining opposed cutouts at said shelves.

* * * * *